(12) United States Patent
Zhang et al.

(10) Patent No.: US 7,914,665 B2
(45) Date of Patent: Mar. 29, 2011

(54) METHOD FOR MAKING A LUBRICATING OIL WITH IMPROVED LOW TEMPERATURE PROPERTIES

(75) Inventors: Lei Zhang, Vienna, VA (US); Elizabeth Stavens, Seabrook, TX (US); Lisa I-Ching Yeh, Marlton, NJ (US); Ian A. Cody, Annandale, NJ (US); William J. Murphy, Baton Rouge, LA (US); Thomas R. Palmer, Bethlehem, PA (US)

(73) Assignee: ExxonMobil Research and Engineering Company, Annandale, NJ (US)

( * ) Notice: Subject to any disclaimer, the term of this patent is extended or adjusted under 35 U.S.C. 154(b) by 142 days.

(21) Appl. No.: 11/667,236

(22) PCT Filed: Nov. 14, 2005

(86) PCT No.: PCT/US2005/041207
§ 371 (c)(1),
(2), (4) Date: Oct. 3, 2007

(87) PCT Pub. No.: WO2006/055500
PCT Pub. Date: May 26, 2006

(65) Prior Publication Data
US 2008/0116108 A1     May 22, 2008

(51) Int. Cl.
*C10G 29/20*     (2006.01)
*C10G 47/02*     (2006.01)

(52) U.S. Cl. .............. 208/28; 208/33; 208/36; 208/108; 208/27

(58) Field of Classification Search ............. 208/18, 208/28, 33, 36
See application file for complete search history.

(56) References Cited

U.S. PATENT DOCUMENTS

| | | | |
|---|---|---|---|
| 3,539,498 A | 11/1970 | Morris et al. | |
| 4,181,598 A | 1/1980 | Gillespie et al. | |
| 4,622,130 A | 11/1986 | Stem et al. | |
| 4,867,862 A | 9/1989 | Ziemer et al. | |
| 6,475,960 B1 * | 11/2002 | Berlowitz et al. | 508/110 |
| 2004/0072676 A1 * | 4/2004 | Bishop et al. | 502/64 |

FOREIGN PATENT DOCUMENTS

| GB | 2 386 608 A | 9/2003 |
|---|---|---|
| WO | WO 99/41335 A | 8/1999 |
| WO | WO 2004/053030 A | 6/2004 |

* cited by examiner

*Primary Examiner* — Tam M Nguyen
(74) *Attorney, Agent, or Firm* — Robert A Migliorini (57) ABSTRACT

The invention relates to a process for preparing lube oil basestocks from lube oil boiling range feeds. More particularly, the present invention is directed toward a process wherein a wax containing feed is solvent dewaxed to produce at least a partially dewaxed lube oil boiling range stream, which is hydrodewaxed to produce a first lube basestock. The first lube basestock is added to an independently selected second lube basestock and additives to make a lubricating oil.

17 Claims, 1 Drawing Sheet

*FIGURE*

METHOD FOR MAKING A LUBRICATING OIL WITH IMPROVED LOW TEMPERATURE PROPERTIES

FIELD OF THE INVENTION

This invention relates to a process for preparing lube oil basestocks from lube oil boiling range feeds. More particularly, the present invention is directed toward a process wherein a wax-containing feed is solvent dewaxed to produce at least a partially dewaxed lube oil boiling range stream, which is hydrodewaxed to produce a first lube basestock. The first lube basestock is added to an independently selected second lube basestock and additives to make a lubricating oil.

BACKGROUND OF THE INVENTION

It has long been recognized that one of the most valuable products generated through the refining of crude mineral oils is lubricating oils. It is common practice to recover lubricating oil basestocks by solvent extracting, with a selective solvent, undesirable components such as sulfur compounds, oxygenated compounds, and aromatics from straight distillates. However, with the decline in the availability of paraffinic base crudes, and a corresponding increase in the proportion of naphthenic and asphaltic base crudes, it is becoming increasingly difficult to meet the demand for lubricating oil basestocks, or base oils.

Other conventional techniques for preparing basestocks include hydroconversion and solvent extraction. For example, U.S. Pat. No. 5,935,416, Cody et al., teaches a process wherein a lube oil boiling range feed is solvent extracted, stripped, and passed through two hydroconversion zones prior to hydrofinishing and then dewaxing, thus producing a lubricating oil basestock. Other processes such as U.S. Pat. No. 5,171,422, Kirker et al., and U.S. Pat. No. 6,217,747 B1, Chang et al., teach a process whereby a high quality lubricating oil basestock is produced by subjecting a high boiling range hydrocarbon stream to hydrocracking conditions. The U.S. Pat. No. 5,171,422 patent utilizes a high silica content zeolite catalyst of the faujasite type to produce a hydrocrackate product, and the U.S. Pat. No. 6,217,747 patent utilizes a hydrocracking catalyst comprising a hydrogenation/dehydrogenation component and an acidic solid component modified with an oxyanion to produce a hydrocrackate product. The hydrocrackate product is then processed to produce a lubricating oil basestock. One of the many drawbacks of lubricating oil refining utilizing hydroconversion, hydrocracking or solvent extraction is that such processes typically require severe operating conditions such as high pressure and temperature or high solvent:oil ratios and high extraction temperatures to produce high basestock qualities. Further, hydroconversion, hydrocracking or solvent extraction typically involve expensive operating conditions and low yields.

Further, even though hydroconversion, hydrocracking or solvent extraction can be used in lubricating oil refining, most lubricating oil feeds must also be dewaxed in order to produce lubricating oils which will remain fluid down to the lowest temperature of use. Dewaxing is the process of separating or converting hydrocarbons which solidify readily (i.e., waxes) in petroleum fractions. The catalytic dewaxing of wax and waxy feeds boiling in the lubricating oil range and catalysts useful in such processes are well known in the art. Generally these processes utilize catalysts comprising a molecular sieve component and a component selected from the Group VIII and/or Group VIB metals. Many examples of hydrodewaxing processes and catalysts commonly used are known in the art such as, for example, the processes and catalysts disclosed in U.S. Pat. No. 4,563,266, Hopkins et al., and U.S. Pat. No. 5,075,269, Degnan, et al.

It has also been proposed to solvent dewax a lube oil boiling range feed followed by catalytically dewaxing the solvent dewaxed lube oil stream. Examples of these processes can be found in U.S. Pat. No. 3,755,138, Chen et al., U.S. Pat. No. 4,622,130, Stephen C. Stem, and European Publication Number 0271265. However, processes such as those disclosed therein, and in similar processes, suffer from low yields, sometimes on the order of 50%, based on the lube oil feed. These processes also typically suffer from the catalytic dewaxing step altering key basestock properties such as viscosity and viscosity index.

While basestock quality is improving, further improvements in many properties, such as low temperature quality, as well as combinations of properties, such as superior low temperature fluidity at low product volatility, continue to challenge the industry. Benefits in low temperature performance would be beneficial for a wide range of formulated lubricants and would be particularly advantageous for passenger vehicle crankcase oils, automatic transmission fluids, automotive gear oils, hydraulic fluids, and commercial vehicle crankcase oils.

Low temperature quality for basestocks and base oils have historically been controlled using bulk property measurements such as pour point measured on the basestock, base oils, or formulated oil composition. However, small amounts of residual wax may not impact this bulk property measurement and, thus, small amounts of residual wax may go undetected through this simple analysis. This small amount of residual wax, however, does impact performance and can lead to issues such as crankcase oil gelling and loss of fluidity. Operating an engine in this scenario can lead to and has led to engine damage. Hence, the Mini-Rotary Viscometer (MRV) test was established to protect engines under cold weather conditions. The MRV test temperature is set by the Society of Automotive Engineers (SAE) J-300 Viscosity Classification system for each multigrade engine oil grade.

To improve the low temperature performance as measured by the MRV or other tests sensitive to very small amounts of residual wax, refineries utilizing solvent dewaxing can dewax to lower pour points. While this can be effective, improvements are still needed. Catalytic dewaxing, a relatively newer processing approach, is often more effective than solvent dewaxing, especially for the light and medium neutral stocks. However, many existing refineries in operation today utilize solvent dewaxing only and do not have the equipment available for catalytic dewaxing which often requires high quantities of pure hydrogen provided at high pressure and pretreatment of feed to remove S and N.

Thus, as the demand for quality lube oil basestock continues to increase, the search for new and different processes, catalysts, and catalyst systems that exhibit improved activity, increased yields, selectivity and/or longevity is a continuous, ongoing exercise. Therefore, there is a need in the lube oil market to provide processes that can produce lube oil basestocks in ever-increasing yields that meet the demand for increased fuel economy, reduced emissions, etc.

BRIEF DESCRIPTION OF THE FIGURE

The FIGURE demonstrates the 370° C.+ Gas Chromatograph Distillation ("GCD") Conversion as a Function of Reaction Temperature.

SUMMARY OF THE INVENTION

Figure 1:
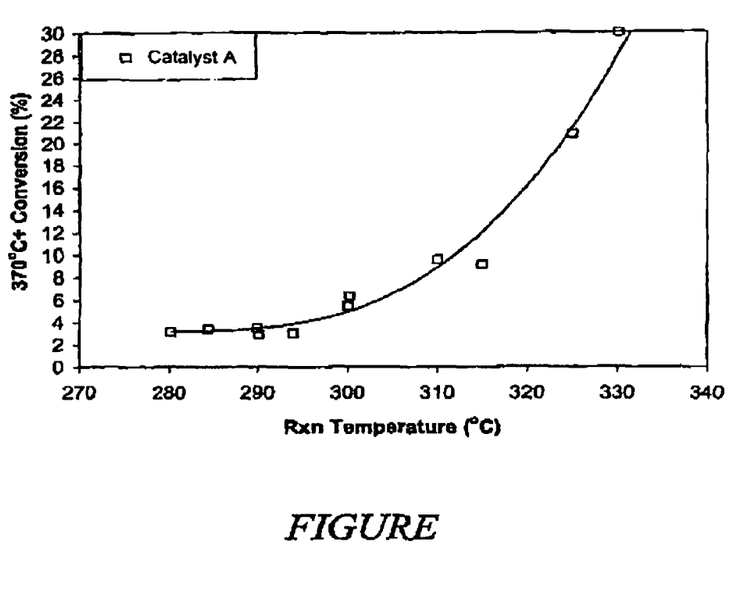

In an embodiment, the invention relates to a method for making a finished lubricating oil, comprising adding to a first basestock at least a second basestock and at least one additive, the second base stock being independently selected from the first basestock, wherein the first base stock is made by:
 a) solvent dewaxing a lube oil boiling range feed in a solvent dewaxing stage operated under effective solvent dewaxing conditions thereby producing at least a partially dewaxed feed; and
 b) contacting the partially dewaxed feed with a catalytically effective amount of a hydrodewaxing catalyst in the presence of a hydrogen-containing treat gas in a reaction stage operated under effective hydrodewaxing conditions thereby producing a reaction product comprising the first basestock.

In an another embodiment, the invention relates to a method for making a finished lubricating oil, comprising adding to a first basestock at least a second basestock and at least one additive, the second base stock being independently selected from the first basestock, wherein the first base stock is made by:
 a) separating a wax from the feed; and then
 b) contacting the dewaxed feed with a catalytically effective amount of a hydrodewaxing catalyst in the presence of a hydrogen-containing treat gas in a reaction stage operated under effective hydrodewaxing conditions thereby producing a reaction product comprising the first basestock.

In yet an another embodiment, the invention relates to a method for making a finished lubricating oil, comprising adding to a first basestock at least a second basestock and at least one additive, the second base stock being independently selected from the first basestock, wherein the first base stock is made by contacting the feed. with a catalytically effective amount of a hydrodewaxing catalyst in the presence of a hydrogen-containing treat gas in a reaction stage operated under effective hydrodewaxing conditions thereby producing a reaction product comprising the first basestock, wherein the first basestock has at least one of (i) an increased VI, (ii) improved ASTM color, (iii) increased kinematic viscosity, (iv) decreased pour point, and (v) decreased cloud point compared to the feed, and wherein no wax is separated during the making of the first basestock.

In another embodiment, the lube oil boiling range feed to the solvent dewaxing is a raffinate obtained from solvent extraction. In a related embodiment, the raffinate is a hydroprocessed raffinate.

In yet another embodiment, the lube oil boiling range feed is a hydrocrackate.

In another embodiment, the first basestock has a kinematic viscosity less than that of the second basestock, the kinematic viscosity being measured at about 100° C.

In another embodiment, the lubricating oil has an MRV ranging from about 1,000 cP to about 75,000 cP, preferably from about 5,000 cP to about 50,000 cP, and more preferably from about 10,000 cP to about 40,000 cP. In a related embodiment, the lubricating oil's MRV is less than about 75,000 cP, preferably less than about 50,000 cP, and more preferably less than about 40,000 cP. The lubricating oil preferably has a pour point ranging from about 1° C. to about −33° C., preferably from about 0° C. to about −30° C., and more preferably from about −15° C. to about −25° C. In an embodiment, the pour point of the lubricating oil is less than about 0° C.

Another embodiment comprises the lubricating oil made by the methods described herein.

DETAILED DESCRIPTION OF THE INVENTION

The present invention relates to a process for making finished lubricating oils from basestocks in the lube oil boiling range. In a first step, a lube oil boiling range feed is solvent dewaxed under conditions effective at producing at least a partially dewaxed feed. At least a portion of the partially dewaxed feed is then contacted with a catalytically effective amount of a hydrodewaxing catalyst in the presence of a hydrogen-containing treat gas in a reaction stage operated under effective hydrodewaxing conditions in order to produce a reaction product comprising a first basestock. The first basestock is added to or combined with a second basestock and one or more additives in order to make the finished lubricating oil. It has been discovered that a lubricating oil with improved low temperature properties results when the first basestock is made by a process comprising a solvent dewaxing step followed by a hydrodewaxing step, instead of solvent dewaxing alone, or by hydrodewaxing followed by solvent dewaxing. In other words, it has been discovered that a first basestock made by one of the alternative processes (i.e., hydrodewaxing followed by solvent dewaxing or solvent dewaxing alone) which is then added to additives and a second basestock to make a finished lubricating oil, will result in a finished lubricating oil with low temperature properties such as MRV that are not as desirable as those of a finished lubricating oil made in accordance with the invention. This is the case even when the alternative processes are regulated so that the conventionally-measured physical properties of the first basestock (e.g., pour point, viscosity index, kinematic viscosity, color, etc.) are the same as in a first basestock made in accordance with the invention.

While the first basestock can be made by hydroprocessing only, such processes may not be suitable when a wax product is desired since the wax product is made as a consequence of solvent dewaxing. But where wax production is not desired, an embodiment of the invention relates to making the first basestock by a process that uses hydrodewaxing but does not use solvent dewaxing, preferably a mild hydrodewaxing, and more preferably a mild hydrodewaxing process where the hydrodewaxed product has at least one of (i) an increased VI, (ii) improved ASTM color, (iii) increased kinematic viscosity, (iv) decreased pour point, and (v) decreased cloud point compared to the feed to the hydrodewaxing step or stage, preferably at least two of (i) through (v), and more preferably at least three of (i) through (v).

Suitable lube oil boiling range feeds for processes for making the first and/or second basestock include wax-containing feeds that boil in the lubricating oil range. These lube oil boiling range feeds typically having a 10% distillation point greater than about 650° F. (343° C.), measured by ASTM D 86 or ASTM 2887, and are derived from mineral sources, synthetic sources, or a mixture of the two. Non-limiting examples of suitable lubricating oil feeds include those derived from sources such as oils derived from solvent refining processes such as raffinates, partially solvent dewaxed oils, deasphalted oils, distillates, vacuum gas oils, coker gas oils, slack waxes, foots oils and the like, dewaxed oils, automatic transmission fluid feeds, and Fischer-Tropsch waxes.

Suitable lube oil boiling range feeds may also have high contents of nitrogen and sulfur contaminants. Feeds containing up to about 0.2 wt. % of nitrogen, based on feed and up to about 3.0 wt. % of sulfur can be processed in the present process. Feeds having a high wax content typically have high viscosity indexes of up to 200 or more. Sulfur and nitrogen contents may be measured by standard ASTM methods; for example, D5453 and D4629, respectively.

In one embodiment the first and second basestocks are hydroprocessed prior to dewaxing. For example, a lube oil boiling range feed is first contacted in a first reaction stage with a hydroprocessing catalyst, in the presence of a hydrogen-containing treat gas, under effective hydroprocessing conditions thereby producing at least a liquid hydroprocessed lube oil product. The hydroprocessed lube oil product is then conducted to the solvent dewaxing zone. In an embodiment of the instant invention, separation stages are employed to separate gaseous and liquid reaction products, dewaxing solvent from the dewaxed product, etc.

The second basestock is generally different from and independently selected from the first basestock. Although the second basestock can be made the same way as the first base stock, it need not be. In an embodiment the second basestock is made by conventional basestock manufacturing processes, such as those described in U.S. Pat. Nos. 5,935,417 and 6,099,719, which are incorporated by reference herein. Those skilled in the art of lubricating oil manufacturing are aware of methods for blending two or more basestocks and additives in order to make a finished lubricating oil having targeted properties, such as a targeted viscosity, viscosity index, pour point, etc. Accordingly, if the properties and amount of first basestock were known, it is conventional to calculate the amounts and properties of the second basestock and additives that will be needed to form a finished lubricating oil having the targeted properties. The second basestock can be one or more conventional basestocks such as EHC 35™, EHC 45™, EHC 50™, EHC 60™, EHC 80™, and/or EHC 110™ basestock, all available from ExxonMobil. Generally a major amount of the first basestock is combined with a minor amount of the second basestock. In an embodiment, about 80 wt. % of the first basestock is added to about 20 wt. % of the second basestock, the wt. % being based on the combined weight of the first and second basestocks. Additives are added to the basestocks, generally to improve a physical property of the oil such as viscosity index. Such additives include, e.g., one or more of dispersants, detergents, wear inhibitors, antioxidants, rust inhibitors, demulsifiers, extreme pressure agents, friction modifiers, multifunction additives, viscosity index improvers, pour point depressants, and foam inhibitors.

Generally, a lube oil boiling range feed used to make the first basestock is solvent extracted in a solvent dewaxing stage operated under effective solvent dewaxing conditions thereby producing at least a partially dewaxed feed. The solvent dewaxing process typically involves mixing the lube oil boiling range feed with a dewaxing solvent at atmospheric pressure, separating precipitated wax and recovering the solvent for recycling. The lube oil boiling range feed is mixed with chilled solvent to form an oil-solvent solution and precipitated wax is thereafter separated by, for example, filtration. The temperature and solvent are selected so that the oil is dissolved by the chilled solvent while the wax is precipitated. Thus, one embodiment of the instant invention involves separating, by any suitable separation means, the solvent and partially dewaxed feed, recovering the partially dewaxed feed and conducting the partially dewaxed feed to a hydrodewaxing reaction stage. In a related embodiment, the partially dewaxed feed can be separated, with a first portion conducted to hydrodewaxing and at least a second portion conducted away from the process. It should be noted that because solvent dewaxing typically occurs at atmospheric pressure, it may be necessary to pressurize the partially dewaxed feed prior to the catalytic dewaxing step.

A particularly suitable solvent dewaxing process involves the use of a cooling tower where solvent is prechilled and added incrementally at several points along the height of the cooling tower. The lube oil boiling range feed-solvent mixture is agitated during the chilling step to permit substantially instantaneous mixing of the prechilled solvent with the lube oil boiling range feed. The prechilled solvent is added incrementally along the length of the cooling tower so as to maintain an average chilling rate at or below about 10° F./minute (5.6° C./minute), usually between about 1° F. to about 5° F./minute (0.56 [−17.2]° C. to 2.8[−15]° C./minute). The final temperature of the lube oil boiling range feed-solvent/precipitated wax mixture in the cooling tower will usually he between about 0° F. and about 50° F. (−17.8° C. to 10° C.). The mixture may then be sent to a scraped surface chiller to separate precipitated wax from the mixture.

Effective solvent dewaxing conditions are conditions that are capable of removing at least a portion of the wax contained in the lube oil boiling range feed. Generally, effective solvent dewaxing conditions will include that amount of solvent that when added to the lube oil boiling range feed will be sufficient to provide a liquid:solid weight ratio of about 5:1 to about 20:1 at the dewaxing temperature and a solvent:oil volume ratio between about 1.5:1 to about 5:1. The solvent dewaxing of the lube oil boiling range feed typically results in a partially dewaxed feed having a pour point from about +30° C. to about −20° C.

Representative dewaxing solvents are aliphatic ketones having 3-6 carbon atoms such as methyl ethyl ketone and methyl isobutyl ketone, low molecular weight hydrocarbons such as propane and butane, and mixtures thereof. The solvents may be mixed with other solvents such as benzene, toluene or xylene. Further descriptions of solvent dewaxing process useful herein are disclosed in U.S. Pat. Nos. 3,773,650 and 3,775,288, which are incorporated herein in their entirety.

The partially dewaxed feed may be suitable as a lube basestock, such as the second basestock. However, in an embodiment of the invention, the partially dewaxed feed is subjected to a further catalytic dewaxing step to remove at least a portion of any wax remaining in the partially dewaxed feed. Thus, this step is commonly used to further lower the pour point of the partially dewaxed feed. The sequence of solvent dewaxing followed by catalytic dewaxing is commonly designated as "trim" dewaxing.

Turning now to the hydrodewaxing step, the partially dewaxed feed is contacted with a catalytically effective amount of a hydrodewaxing catalyst in the presence of a hydrogen-containing treat gas in a reaction stage operated under effective hydrodewaxing conditions. Effective hydrodewaxing conditions as used herein includes temperatures between about 200° C. to about 350° C., preferably about 250° C. to about 325° C., more preferably about 250° C. to about 310° C., pressures between about 2,860 to about 20786 kPa (400 to 3000 psig), preferably about 4238 to about 17338 kPa (600 to 2500 psig), preferably about 4238 to about 10443 kPa (600 to 1500 psig) hydrogen treat gas rates of about 89 to about 890 $m^3/m^3$ (500 to 5000 SCF $H_2$/B), preferably about 107 to about 445 $m^3/m^3$ (600 to 2500 SCF $H_2$/B), and liquid hourly space velocities ("LHSV") of about 0.1 to about 10 V/V/hr, preferably about 0.1 to about 5 V/V/hr, more preferably about 0.5 to about 2 V/V/hr. In an embodiment, the hydrodewaxing reaction stage is operated under mild (i.e., less severe) hydrodewaxing conditions to convert trace paraffins; that impair low temperature properties of the solvent dewaxed fraction at a low yield loss while still maintaining the physical basestock properties such as pour point, viscosity, viscosity index ("VI"), and volatility of the partially dewaxed feed resulting from the solvent-dewaxing step. In a related embodiment, effective hydrodewaxing conditions include conditions that result in one or more of (i) a lube basestock having a VI within about 0 to about 20 points of the partially dewaxed feed, preferably about 0 to about 10 VI points, more preferably about 0 to about 5 VI points, most preferably about 0 to about 2 VI points; (ii) conditions that result in a lube basestock having a pour point within about 0 to about −50° C. of the partially dewaxed feed, preferably about 0° C. to about −30° C., more preferably about 0° C. to about −10" C., most preferably about 0° C. to about −3° C.; and (iii) a yield loss of about 0 to about 20 wt. %, based on the weight of the partially dewaxed feed, preferably about 0 to about 15 wt. %, more preferably about 0 to about 10 wt. %, most preferably about 0 to about 5 wt. %.

In an embodiment, the effective hydrodewaxing conditions are generally mild conditions that are used to improve the low temperature properties of the lube basestock while minimizing any negative effects typically associated with hydrodewaxing such as, for example, yield loss.

Hydrodewaxing catalysts suitable for use herein can be crystalline, amorphous, partly crystalline, partly amorphous, disordered but neither fully crystalline nor fully amorphous, and mixtures thereof. Amorphous hydrodewaxing catalysts include alumina, fluorided alumina, silica-alumina, and fluorided silica-alumina. Such catalysts are described, for example, in U.S. Pat. Nos. 4,900,707 and 6,383,366.

Crystalline materials are molecular sieves that contain at least one 10- or 12-ring channel and may be based on aluminosilicates (zeolites) or on aluminophosphates such as silicoaluminophosphates (SAPOs) and magnealuminophosphates (MAPOs). Molecular sieves suitable for use herein contain at least one 10- or 12-ring channel. Examples of such zeolites include ZSM-22, ZSM-23, ZSM-35, ZSM-48, ZSM-57, ferrierite, ITQ-13, MCM-68 and MCM-71. Examples of aluminophosphates containing at least one 10-ring channel include ECR-42. Examples of molecular sieves containing 12-ring channels include zeolite beta, and MCM-68. Some molecular sieves suitable for use herein are described in U.S. Pat. Nos. 5,246,566, 5,282,958, 4,975,177, 4,397,827, 4,585,747, 5,075,269 and 4,440,871. MCM-68 is described in U.S. Pat. No. 6,310,265. MCM-71 and ITQ-13 are described in PCT published applications nos. WO02/42207 and WO00/78677. ECR-42 is disclosed in U.S. Pat. No. 6,303,534. Suitable SAPOs for use herein include SAPO-11, SAPO-31, SAPO-41, and suitable MAPOs include MAPO-11. SSZ-31 is also a catalyst that can be effectively used herein. It should be noted that hydrodewaxing catalysts do not require a hydrogenation function, and thus do not require a hydrogenation metal deposited thereon.

In an embodiment, the hydrodewaxing catalyst is a zeolite. Preferred zeolite hydrodewaxing catalysts suitable for use herein include ZSM-48, ZSM-22 and ZSM-23. Especially preferred is ZSM-48. The molecular sieves are in the hydrogen form.

In an embodiment, the hydrodewaxing catalysts are bifunctional, i.e., they are loaded with at least one metal hydrogenation component, which is selected from Group VI metals, Group VIII metals, and mixtures thereof. Preferred metals are selected from Group VIII metals. Especially preferred are Group VIII noble metals such as Pt, Pd or mixtures thereof. In an embodiment, the metals are loaded at the rate of about 0.1 to 3 about 0 wt. %, based on the weight of the catalyst. Catalyst preparation and metal loading methods are described, for example, in U.S. Pat. No. 6,294,077, and include, for example, ion exchange and impregnation using decomposable metal salts. Metal dispersion techniques and catalyst particle size control techniques are described in U.S. Pat. No. 5,282,958. Catalysts with small particle size and well-dispersed metal are preferred.

The molecular sieves are typically composited with binder materials which are resistant to high temperatures which may be employed under hydrodewaxing conditions to form a finished hydrodewaxing catalyst or may be binderless (self bound). The binder materials are usually inorganic oxides such as silica, alumina, silica-aluminas, binary combinations of silicas with other metal oxides such as titania, magnesia, thoria, zirconia and the like and tertiary combinations of these oxides such as silica-alumina-thoria and silica-alumina magnesia. The amount of molecular sieve in the finished hydrodewaxing catalyst is from about 10 to about 100 wt. %, preferably about 35 to about 100 wt. %, based on catalyst. Such catalysts are formed by methods such spray drying, extrusion and the like. The hydrodewaxing catalyst may be used in the sulfided or unsulfided form, and is preferably in the sulfided form for metal-containing hydrodewaxing catalysts.

In an embodiment, the hydrodewaxing reaction stage comprises one or more fixed bed reactors or reaction zones, each of which can comprise one or more catalyst beds of the same or different catalyst. Although other types of catalyst beds can be used, fixed beds are preferred. Such other types of catalyst beds include fluidized beds, ebullating beds, slurry beds, and moving beds. Interstage cooling or heating between reactors, reaction zones, or between catalyst beds in the same reactor, can be employed. A portion of any heat generated during hydrodewaxing can be recovered. Where this heat recovery option is not available, conventional cooling may be performed through cooling utilities such as cooling water or air, or through use of a hydrogen quench stream. In this manner, optimum reaction temperatures can be more easily maintained.

Hydrogen-containing treat gases suitable for use in the hydrodewaxing reaction stage can be comprised of substantially pure hydrogen or can be mixtures of other components typically found in refinery hydrogen streams. However, it is preferred that the hydrogen-containing treat gas stream contains little, more preferably no, hydrogen sulfide. The hydrogen-containing treat gas purity should be at least about 50% by volume hydrogen, preferably at least about 75% by volume hydrogen, and more preferably at least about 90% by volume hydrogen for best results.

The contacting of the partially dewaxed feed with the hydrodewaxing catalyst results in a reaction product comprising at least a gaseous product and a liquid product, wherein the liquid product comprises a lube basestock. Thus, in one embodiment the hydrodewaxing stage product is separated into at least the gaseous product and the liquid product comprising a lube basestock, and the liquid product comprising a lube basestock is recovered. The means by which the hydrodewaxing stage reaction product is separated is not critical and may be performed by any means capable of separating gaseous and liquid reaction products such as, for example, flash or knock-out drums, and/or stripping.

The liquid product comprising a lube basestock recovered may be used in as the first basestock and/or second basestock in blending a finished lubricating oil. One or more fractions can be separated and conducted away from the process for storage and/or further processing, such as to provide various additional lube oil basestocks. Depending on their physical and chemical properties, which can be measured conventionally, such separated basestocks may be useful as the first basestock, the second basestock, or in a variety of applications including blending engine oils, including finished passenger car motor oils, and/or industrial oils.

Thus, in an embodiment, the liquid product comprising a lube basestock recovered from the hydrodewaxing reaction stage can be fractionated to produce at least two product streams, at least one of which is suitable as the first lube basestock. The form of fractionation used herein is not critical and can be any fractionation means. Non-limiting examples of suitable fractionation means include atmospheric and vacuum. It should be noted that the number of lube basestocks, and their weight, depends on the operating conditions, e.g., separation boiling point, selected for the fractionation means. In an embodiment, at least one such fraction produced by fractionating the hydrodewaxed liquid product is a lube basestock suitable for as the first basestock in formulating a finished lubricant, such as a 5W30 passenger car motor oil.

Another embodiment of the instant invention involves contacting a lube oil boiling range feed in a first reaction stage in the presence of a hydrogen-containing treat gas with a hydroprocessing catalyst under effective hydroprocessing conditions. Hydrogen-containing treat gases suitable for use in the hydroprocessing reaction stage can be any hydrogen-containing treat gas suitable for use in the hydrodewaxing stage. The contacting of the lube oil boiling range feed with the hydroprocessing catalyst produces a first stage reaction product comprising a first stage gaseous product and a first stage liquid product comprising a hydroprocessed lube oil product. Hydroprocessing, as used herein, is meant to refer to processes in which hydrogen reacts with a hydrocarbonaceous feed and a catalyst designed to cause the desired reaction. Non-limiting examples of hydroprocessing processes include hydrocracking; hydrotreating to remove heteroatoms, such as sulfur, nitrogen, and oxygen; hydrogenation of aromatics; hydroisomerization and/or catalytic dewaxing; and demetallation of heavy streams. It is preferred that the hydroprocessing be selected from hydrocracking, hydrotreating and mixtures thereof, i.e., hydrocracking followed by hydrotreating or hydrotreating followed by hydrocracking.

Various kinds of feed pre-treatments and product post treatments can be used with the invention, such as an optional hydroprocessing stage or step. Hydroprocessing can occur before dewaxing, after dewaxing, and/or between solvent dewaxing and hydrodewaxing. For example, in an embodiment, the feed to the solvent dewaxing step can be a hydroprocessed feed. In this embodiment, any suitable hydroprocessing catalyst effective at causing the desired reaction can be used, i.e., if hydrocracking is chosen as the hydroprocessing reaction, any hydrocracking catalyst can be used, etc. Further, effective hydroprocessing conditions are conditions that, when coupled with the selected catalyst, are effective at carrying out the desired reaction. The hydroprocessing reaction stage can be comprised of one or more fixed bed reactors or reaction zones each of which can comprise one or more catalyst beds of the same or different catalyst. Although other types of catalyst beds can be used, fixed beds are preferred. Such other types of catalyst beds include fluidized beds, ebullating beds, slurry beds, and moving beds. Interstage cooling or heating between reactors, reaction zones, or between catalyst beds in the same reactor, can be employed. A portion of any heat generated during hydroprocessing can be recovered. Where this heat recovery option is not available, conventional cooling may be performed through cooling utilities such as cooling water or air, or through use of a hydrogen quench stream. In this manner, optimum reaction temperatures can be more easily maintained.

When hydroprocessing is used before solvent dewaxing, the hydroprocessing produces a first stage reaction product comprising a first stage gaseous product and a first stage liquid product comprising a hydroprocessed lube oil product. The first stage reaction product can be conducted directly to the solvent dewaxing stage or conducted to a separation stage to separate the first stage gaseous reaction products from the first stage liquid product. It is preferred that the first stage reaction product be stripped in a stripping stage prior to the solvent dewaxing stage. Stripping can be by conventional means such as flash drums or fractionators. It is preferred that the first stage reaction be stripped by contacting it in a stripping tower with suitable stripping gas.

In yet another embodiment the lube oil boiling range feed is optionally solvent extracted prior to the solvent dewaxing stage. Solvent extraction can be used alone or in combination with the optional hydroprocessing in order to, e.g., increase the viscosity index in the lube oil feed following a loss of viscosity index during solvent extraction. The solvent extraction, when used, can occur before or after the optional hydroprocessing stage. Thus, in an embodiment, the feed to the solvent dewaxing stage is a raffinate, preferably a hydroprocessed raffinate. In this embodiment, a lubricating oil feed is extracted in a solvent extraction zone with an extraction solvent under conditions effective at producing at least an aromatics-lean raffinate solution containing extraction solvent. At least a portion of the extraction solvent is then removed from the aromatics-lean raffinate solution to produce at least a lube oil boiling range raffinate feed, which, following optional hydroprocessing when used, is conducted to the solvent dewaxing step.

The solvent extraction process selectively dissolves the aromatic components in an aromatics-rich extract solution while leaving the more paraffinic components in the "aromatics-lean raffinate solution". Naphthenes are distributed between the extract and raffinate phases. Typical solvents for solvent extraction include phenol, furfural and N-methylpyrrolidone. By controlling the solvent to oil ratio, extraction temperature and method of contacting distillate to be extracted with solvent, one can control the degree of separation between the extract and raffinate phases. The solvent extraction process, solvent, and process conditions used herein are not critical to the instant invention and can be any solvent extraction process, including conventional processes.

The above description is directed to preferred embodiments of the present invention. Those skilled in the art will recognize that other embodiments that are equally effective could be devised for carrying out the spirit of this invention.

EXAMPLES

Example 1

Catalysts

The hydrodewaxing catalyst used to make the first basestock can be, for example, a bi-functional hydrodewaxing catalyst or a hydrodewaxing ("HDW") catalyst containing no metal hydrogenation function. The properties of the catalysts used, and the amount employed, in the examples herein are outlined in Table 1 below. These catalysts included a conventional, commercially-available, non-metal HDW catalyst (H-ZSM-48/$Al_2O_3$) ("Catalyst B"). Catalyst B was formed into $\frac{1}{16}$-inch (1.6-mm) quadrulobe extrudates that contained 65% ZSM-48 crystals bound with 35% alumina. A bi-functional catalyst suitable for use in the present invention ("Catalyst A") was formed by impregnating the extrudates of Catalyst B using platinum tetraammine nitrate. Catalyst C was formed using self-bound H-ZSM-5 extrudates.

TABLE 1

Hydrodewaxing Catalyst Properties

| Catalyst Name | Catalyst A | Catalyst B | Catalyst C |
|---|---|---|---|
| Pt loading (%) | 0.62 | 0 | 0 |
| H/Pt | 1.16 | N/A | N/A |
| Support | ZSM-48 | H-ZSM-48 | H-ZSM-5 |
| Binder | $Al_2O_3$ | $Al_2O_3$ | N/A |
| Surface Area ($m^2/g$) | 247 | 239 | N/A |
| Alpha | 24 | 20 | 47 |
| Catalyst Volume ($cm^3$) | 10 | 5 | 5 |
| Pre-sulfidation | Yes | No | No |

Example 2

Reactor Preparation and Operating Procedure

A solvent dewaxed feed having the properties outlined in Table 2 was obtained by solvent dewaxing a lubricating oil boiling range raffinate obtained from an aromatics extraction process. Three portions of the solvent dewaxed feed were each separately hydrodewaxed using Catalyst A, Catalyst B, and Catalyst C respectively. The hydrodewaxing was conducted using a continuous catalyst testing unit composed of a liquid feed system with an ISCO syringe pump, a fixed-bed tubular reactor with a three-zone furnace, liquid product collection, and an on-line MTI GC for gas analysis. Either about 5 $cm^3$ or about 10 $cm^3$ of catalyst volume (see Table 1) was charged in a down-flow ⅜-inch (9.5-mm) stainless steel reactor containing a ⅛-inch (3.2-mm) thermowell, as shown in the Table. After the unit was pressure tested, the catalyst was dried at 300° C. for 2 hours with 250 cc/min $N_2$ at ambient pressure. If pre-sulfidation of the catalyst was required, 2% (vol.) $H_2S$ in hydrogen was flowed through the catalyst bed at 100 sccm for 1 hour. Upon completion of the catalyst treatment, the reactor was cooled to 150° C., the unit pressure was set to 1,000 psig (6,996 kPa) by adjusting the Mity-Mite back-pressure regulator and the gas flow was switched from $N_2$ to $H_2$. The liquid solvent dewaxed feed described in Table 2 was introduced into the reactor at the desired liquid hourly space velocity (LHSV). Once the liquid solvent dewaxed feed reached the downstream knockout pot, the reactor temperature was increased to the target value. A material balance (MB) was initiated once the unit was lined out for 6 hours. The total liquid product (TLP) was collected in the MB dropout pot. Gas samples were analyzed with an on-line HP MTI gas chromatograph (GC) equipped with both TCD and FID detectors. A series of runs were performed to understand the catalyst activity/product properties as function of the process variables, such as LHSV and process temperature. The TLP product from each balance was cut at 370° C. by batch distillation. The properties of 370° C.+ dewaxed oil were analyzed.

TABLE 2

Solvent Dewaxed Feed Properties

| | |
|---|---|
| Density, g/cc | 0.844 |
| Boiling Range 2% to 98% off, ° F. (° C.) | 690-910 (366-488) |
| Kinematic Viscosity at 40° C., cSt | 23.3 |
| Kinematic Viscosity at 100° C., cSt | 4.6 |
| Viscosity Index | 114 |
| Pour Point (ISL), ° C. | −18 |
| UV Total Aromatics, mmol/kg | 18.5 |

TABLE 2-continued

Solvent Dewaxed Feed Properties

| | |
|---|---|
| Saybolt Color | >+30 |
| GCD Noack Volatility, wt. % | 15.2 |
| Sulfur, wppm | <10 |
| Nitrogen, wppm | <1 |
| CCS (formulated 5W30 engine oil), cP | 5,790 |
| MRV (formulated 5W30 engine oil), cP | 36,211 |

Example 3

Hydrodewaxing Using Catalyst B

The solvent dewaxed feed described in Table 2 above was hydrodewaxed using Catalyst B in accordance with the procedure described in Example 2 at the following conditions: reactor temperature ranging from about 270° C. to about 350° C., total pressure of about 1,000 psig (6,996 kPa), liquid rate of about 10 $cm^3$/hr, $H_2$ circulation rate of about 2,500 scf/bbl (445 $m^3/m^3$), and LHSV of about 2 $hr^{-1}$. Table 3 summarizes the physical properties of the lube product obtained at a temperature of 300° C. using Catalyst B. The product exhibited increased aromatics, and poorer color for a 1° C. pour point change from the solvent dewaxed feed, a 1 VI loss from the feed, and constant Noack volatility. A portion of the HDW basestock obtained from the hydrodewaxing (the first basestock) was added to a second basestock and conventional additives including a detergent/inhibitor, a viscosity index improver, and a pour point depressant to formulate a 5W-30 passenger car motor oil ("PCMO"), which was then tested for cold flow testing including MRV. The MRV results on the formulated 5W-30 lubricating oil (also called "engine oil") are included in Table 3.

As seen in Table 3, with minimal changes to basestock physical properties (a 1° C. change in pour point, which falls within the accuracy of the pour point measurement, and a loss of 1 VI, again within the accuracy of the VI measurement) an 18% decrease in MRV was achieved with a 4.8% yield loss in HDW with the Catalyst B.

TABLE 3

HDW Basestock Properties (Catalyst B)

| Physical Property | Feed | HDW Basestock (Catalyst B) |
|---|---|---|
| 370° C. + Yield, % on SDW feed | 97.5 | 92.7 |
| Kinematic Viscosity at 40° C., cSt | 23.3 | 23.3 |
| Kinematic Viscosity at 100° C., cSt | 4.6 | 4.6 |
| Viscosity Index | 114 | 113 |
| Pour Point (ISL), ° C. | −18 | −19 |
| UV Total Aromatics, mmol/kg | 18.5 | 27.5 |
| Saybolt Color | >+30 | 9 |
| GCD Noack Volatility, wt. % | 15.2 | 15.4 |
| MRV (formulated 5W30 engine oil), cP | 36,211 | 29,600 |

In Example 3, samples were analyzed using $^{13}C$ NMR to observe compositional changes between the solvent dewaxed feed and the hydrodewaxed product. Table 4 highlights the key $^{13}C$ NMR results of the solvent dewaxed feed versus the HDW basestock.

TABLE 4

13C NMR Data of Trim-HDW Basestock (Catalyst B)

| NMR Measurement | Solvent Dewaxed Feed | HDW Basestock (Catalyst B) |
|---|---|---|
| Epsilon Carbons, mole % | 13.66 | 13.64 |
| Total Pendant Groups, mole % | 6.25 | 6.17 |
| Carbon # | 36.7 | 37.7 |
| Free Carbon Index | 4.31 | 4.41 |

Decreases in the mole percent of total pendant groups and the increase in the free carbon index all indicate that decreased branching occurred, potentially as a result of cracking.

Example 4

Hydrodewaxing Over Catalyst C

Catalyst C was evaluated using the operating procedure described in Example 2 at the following conditions: a reactor temperature ranging from about 250° C. to about 280° C., a total pressure of about 1000 psig, (6,996 kPa), liquid feed rate of about 10 cm$^3$/hr, H$_2$ circulation rate of about 2,500 scf/bbl (445 m$^3$/m$^3$), and LHSV of about 2 hr$^{-1}$. It should be noted that Catalyst C is known to promote dewaxing by cracking instead of isomerization. Compared with Catalyst B, Catalyst C presented a 45° C. temperature advantage to achieve the desired product physical properties at the same approximate yield loss. Table 5 summarizes the physical properties of the lube fraction of the product obtained at a temperature of 255° C. using Catalyst C. A portion of the HDW basestock obtained from the hydrodewaxing (the first basestock) was added to a second basestock and conventional additives including a detergent/inhibitor, a viscosity index improver, and a pour point depressant to formulate a 5W-30 PCMO, which was then tested for cold flow testing including MRV. The results from the MRV testing on the formulated engine oils are included in Table 5.

TABLE 5

HDW Basestock Properties (Catalyst C)

| Physical Property | Feed | HDW Basestock (Catalyst C) |
|---|---|---|
| 370° C. + Yield, % on SDW feed | 97.5 | 92.8 |
| Kinematic Viscosity at 40° C., cSt | 23.3 | 23.8 |
| Kinematic Viscosity at 100° C., cSt | 4.6 | 4.7 |
| Viscosity Index | 114 | 113 |
| Pour Point (ISL), ° C. | −18 | −20 |
| UV Total Aromatics, mmol/kg | 18.5 | 20.4 |
| Saybolt Color | >+30 | 16 |
| GCD Noack Volatility, wt. % | 15.2 | 15.1 |
| MRV (formulated 5W30 engine oil), cP | 36,211 | 31,400 |

As seen in Table 5, with minimal changes to the basestock physical properties, a 13% decrease in MRV was achieved with a 4.7% yield in mild trim-HDW with the Catalyst C. While an MRV improvement was observed, the MRV improvement is slightly less than that obtained in Example 3 using Catalyst B in the HDW mode at the same approximate yield loss.

Example 5

Hydrodewaxing Using Catalyst A

This example illustrates the improvement in low-temperature properties achievable by hydrodewaxing a solvent-dewaxed feed at mild conditions with Catalyst A. A greater improvement in low temperature performance is observed using bifunctional Catalyst A compared to the improvements obtained using Catalysts B and C in the hydrodewaxing step.

The effectiveness of the present invention using Catalyst A was evaluated using the operating procedure described in Example 2 at the following conditions: a reactor temperature ranging from about 270° C. to about 345° C., a total pressure of about 1,000 psig (6,996 kPa), liquid rate=about 10 cm$^3$/hr, H$_2$ circulation rate of about 2,500 scf/bbl (445 m$^3$/m$^3$), and LHSV of about 1 hr$^{-1}$. The results are summarized in the FIGURE.

The results contained in the FIGURE demonstrate that the 370° C.+ conversion of the solvent dewaxed feed was seen to increase with increasing reactor temperatures. A low yield loss (less than 10 wt. %) could be achieved at a temperature range of 270° C. to 310° C. It is highly desirable to improve basestock properties while maximizing lube yield. At mild process conditions (process temperature of 290° C.), the hydrodewaxed lubricating oil basestock, showed a marginal decrease in pour point from −18° C. to −19° C., compared to the solvent dewaxed feed, while 370° C.+ product yield loss was only 3%, based on the solvent dewaxed feed. In addition, the viscosity index ("VI") and viscosity remained nearly unchanged. Using a bifunctional catalyst for HDW results in the additional benefit of increased aromatics saturation, and, consequently, fewer aromatics in the resulting basestock. For example, the aromatics content of the HDW product is essentially zero. High saturate content, i.e. saturated aromatics, in the lube product provides better oxidation stability and increases the value of the lube oil basestock. Table 6 summarizes the physical properties of the lube fraction of the product with the highest 370° C.+ yield. A portion of the HDW basestock (the first basestock) obtained from the hydrodewaxing was added to a second basestock and conventional additives including a detergent/inhibitor, a viscosity index improver, and a pour point depressant to formulate a 5W-30 PCMO, which was then tested for cold flow testing including mini rotary viscometer (MRV) and cold cracking simulator (CCS). The results from the cold flow testing are included in Table 6.

TABLE 6

HDW Basestock Properties (Catalyst A)

| Physical Property | Feed | HDW Basestock (Catalyst A) |
|---|---|---|
| 370° C. + Yield, % on SDW feed | 97.5 | 94.6 |
| Kinematic Viscosity at 40° C., cSt | 23.3 | 23.7 |
| Kinematic Viscosity at 100° C., cSt | 4.6 | 4.7 |
| Viscosity Index | 114 | 113 |
| Pour Point (ISL), ° C. | −18 | −19 |
| UV Total Aromatics, mmol/kg | 18.5 | 0 |
| Saybolt Color | >+30 | >+30 |
| GCD Noack Volatility, wt. % | 15.2 | 15.3 |
| CCS (formulated 5W30 engine oil), cP | 5790 | 5180 |
| MRV (formulated 5W30 engine oil), cP | 36,211 | 19,624 |

As summarized in Table 6, minimal changes to basestock physical properties (viscosity, VI, pour point, volatility) were observed. However, a 46% decrease in MRV and an 11% decrease in CCS were obtained with less than 3% yield loss in HDW with Catalyst A. As noted above, the aromatic saturation benefit of using the Catalyst A in a HDW mode is clearly reflected by the negligible aromatics content of the hydrodewaxed product. The MRV improvement and yield loss associated with the HDW over Catalyst A are superior to the improvements observed in Example 3 where Catalyst B was employed in the HDW setup as demonstrated by the 46% MRV improvement with <3% yield loss.

$^{13}$C NMR was used to show that mild hydrodewaxing isomerizes the trace paraffins that impair the low temperature, low-shear properties of solvent-dewaxed basestocks to provide exceptional improvements to formulated engine oil cold flow properties. Table 7 highlights the key $^{13}$C NMR results of the feed versus HDW basestock.

TABLE 7

$^{13}$C NMR Data of Hydrodewaxed Basestock(Catalyst A)

| NMR Measurement | Feed | HDW Basestock (Catalyst A) |
|---|---|---|
| Epsilon Carbons, mole % | 13.66 | 13.04 |
| Total Pendant Groups, mole % | 6.25 | 6.58 |
| Pendant Methyl Groups, mole % | 5.00 | 5.30 |
| No. Side Chains/Molecule | 1.97 | 2.03 |
| Carbon Number | 36.7 | 36.5 |
| Free Carbon Index | 4.31 | 4.02 |

Increases in the mole percent of total pendant groups, mole percent of pendant methyl groups, and number of side chains and the decrease observed in the mole percent of epsilon carbons and free carbon index all indicate that increased "branchiness" of lube molecules, likely due to isomerization, has occurred. No significant changes in carbon number (CN) were observed. The trends shown in Table 7 indicate that isomerization is likely the key mechanism behind the extensive improvement observed in engine oil low temperature properties using Catalyst A in a hydrodewaxing, as opposed to the trends in Table 4 which indicate that cracking is the likely the key mechanism behind the 17% improvement in MRV when Catalyst B is used.

Thus, the results contained in Tables 1-7 indicate that the performance of Catalyst B in the hydrodewaxing stage is an improvement over Catalyst C. However, the results also demonstrate that Catalyst A unexpectedly performs significantly better that both Catalysts B and C. Catalyst A produced a product in yields higher than those obtained by using Catalysts B and C. HDW over Catalyst A also produced a product having superior low temperature properties such as CCS and MRV when compared to the products produced from the HDW processes using Catalysts B and C. Further, compared with Catalyst A, Catalyst B resulted in a higher 370° C.+ product yield loss at an equivalent lube pour point target which indicated that zeolite acid function alone was not sufficient to achieve the increased improvement observed with Catalyst A.

Example 6

Properties of the Second Basestock

A second basestock was used with the first basestock to make the 5W-30 PCMOs in examples 3, 4, and 5. A major amount of the first basestock was used with a minor amount of the second basestock, in order to achieve the desired properties in the finished oil. Second basestock properties are set out in Table 8.

TABLE 8

| Physical Property | Second Basestock |
|---|---|
| Kinematic Viscosity at 100° C., cSt | About 5.8 to About 6.2 |
| Viscosity Index | About 113 to About 119 |

TABLE 8-continued

| Physical Property | Second Basestock |
|---|---|
| Pour Point (ISL), ° C. | About −18 |
| GCD Noack Volatility, wt. % | About 9 |

Example 7

Comparative Examples

The samples were prepared by separating three portions of the raffinate of Example 2 for hydrodewaxing using Catalyst A. The first portion was hydrotreated to achieve a pour point of 30° C. in the HDW product, the second to 5° C., and the third to −6° C. Each hydrodewaxed product was then solvent dewaxed to make a basestock with a pour point similar to the pour points of the first basestock of Examples 3, 4, and 5 (i.e., in the range of about −18° C. to about −20° C.), and identified as third, fourth, and fifth basestock respectively.

Three lubricating oil samples were prepared, identified as Comparative Oil 1, Comparative Oil 2, and Comparative Oil 3. Comparative Oil 1 was made by adding the third basestock to the second basestock and conventional additives including a detergent/inhibitor, a viscosity index improver, and a pour point depressant, to formulate a 5W-30 PCMO, which was then tested for MRV viscosity. Comparative Oils 2 and 3 were made in a similar way, but using the fourth and fifth basestocks respectively. MRV results are set out in Table 9.

TABLE 9

| 5W-30 PCMO | Comparative Oil 1 | Comparative Oil 2 | Comparative Oil 3 |
|---|---|---|---|
| MRV (cP) | About 100,000 | About 100,000 | About 90,000 |

It is clear from Table 9 that when the first basestock is made by hydrodewaxing followed by solvent dewaxing, the finished oil's MRV is not improved to the extent that is obtained when the first basestock is made by solvent dewaxing followed by hydrodewaxing.

The invention claimed is:

1. A process to prepare lube basestocks from the lube oil boiling range feedstreams comprising:
 a) solvent dewaxing a lube oil boiling range feedstream in a solvent dewaxing stage operated under effective solvent dewaxing conditions thereby producing at least a partially dewaxed fraction, wherein the solvent dewaxing solvent is selected from the group consisting of methyl ethyl ketone, methyl isobutyl ketone, propane, ethane, and mixtures thereof; and
 b) contacting said partially dewaxed fraction with a hydrodewaxing catalyst in the presence of a hydrogen-containing treat gas in a reaction stage operated under effective mild hydrodewaxing conditions, thereby producing a reaction product comprising at least a gaseous product and liquid product,
 wherein said liquid product comprises a lube basestock, wherein the hydrodewaxing catalyst consists essentially of ZSM-48,
 wherein the effective mild hydrodewaxing conditions include temperatures of from 250° C. to 310° C., pressures of from 4,238 to 10,443 kPa (600 to 1,500 psig), liquid hourly space velocities of from 0.5 to 2 hr$^{-1}$, and hydrogen treat gas rates of 107 to 445 m$^3$/m$^3$ (600 to 2,500 SCF $H_2$/B) to convert trace paraffins remaining in said partially dewaxed fraction, and wherein the lube basestock has a VI within 0 to 2 points of the partially dewaxed fraction, a yield loss of 0 to 5 wt% based on the partially dewaxed fraction, a pour point within 0 to −3° C. of the partially dewaxed fraction, and a mini-rotary viscometry (MRV) value of at least 18% lower than the fully dewaxed fraction using only solvent dewaxing when blended into a finished lubricating oil, wherein said lube oil boiling range feedstreams are selected from raffinates, partially solvent dewaxed oils, deasphalted oils, distillates, vacuum gas oils, coker gas oils, foots oil, and dewaxed oils.

2. The process according to claim 1, wherein said lube oil boiling range feedstreams have a 10% distillation point greater than 650° F. (343° C.), measured by ASTM D 86 or ASTM 2887, and are derived from mineral sources, synthetic sources, or a mixture of the two.

3. The process according to claim 1, wherein said lubricating oil feedstream contains up to 0.2 wt % of nitrogen, based on the lubricating oil feedstream, and up to 3.0 wt % sulfur, based on the lubricating oil feedstream.

4. The process according to claim 1, wherein said hydrodewaxing catalyst further comprises at least one metal hydrogenation component, which is selected from Group VI metals, Group VIII metals, or mixtures thereof.

5. The process according to claim 1, wherein said hydrodewaxing catalyst further comprises a binder material selected from inorganic oxides such as silica, alumina, silica-aluminas, binary combinations of silicas with other metal oxides such as titania, magnesia, thoria, zirconia and the like and tertiary combinations of these oxides such as silica-alumina-thoria and silica-alumina magnesia.

6. The process according to claim 1, wherein said liquid product comprising a lube basestock is fractionated to produce at least two lube basestocks.

7. The process according to claim 1, wherein said process further comprises: a) contacting the lube oil boiling range feedstream in the presence of a hydrogen-containing treat gas with a hydroprocessing catalyst in a hydroprocessing reaction stage operated under effective hydroprocessing conditions thereby producing a hydroprocessed reaction product comprising a hydroprocessing stage gaseous product and a hydroprocessing stage liquid product comprising a hydroprocessed lube oil product; and b) conducting said hydroprocessed reaction product to said solvent dewaxing stage.

8. The process according to claim 7 wherein said hydroprocessing catalyst and said effective hydroprocessing conditions are selected to achieve the hydrocracking of the lube oil boiling range feedstream; hydrotreating of the lube oil boiling range feedstream to remove heteroatoms; and/or hydrogenation of aromatics in the lube oil boiling range feedstream.

9. A process for making lubricating oil, comprising:
a) solvent dewaxing a lube oil boiling range feedstream in a solvent dewaxing stage operated under effective solvent dewaxing conditions thereby producing at least a partially dewaxed fraction, wherein the solvent dewaxing solvent is selected from the group consisting of methyl ethyl ketone, methyl isobutyl ketone, propane, ethane, and mixtures thereof;
b) contacting said partially dewaxed fraction with a hydrodewaxing catalyst in the presence of a hydrogen-containing treat gas in a reaction stage operated under effective mild hydrodewaxing conditions, thereby producing a reaction product comprising a lube basestock;

wherein the hydrodewaxing catalyst consists essentially of ZSM-48, wherein the effective mild hydrodewaxing conditions include temperatures of from 250° C. to 310° C., pressures of from 4,238 to 10,443 kPa (600 to 1,500 psig), liquid hourly space velocities of from 0.5 to 2 hr$^{-1}$, and hydrogen treat gas rates of 107 to 445 m$^3$/m$^3$ (600 to 2,500 SCF $H_2$/B) to convert trace paraffins remaining in said partially dewaxed fraction, and wherein the lube basestock has a VI within 0 to 2 points of the partially dewaxed fraction, a yield loss of 0 to 5 wt % based on the partially dewaxed fraction, a pour point within 0 to −3° C. of the partially dewaxed fraction, and a mini-rotary viscometry (MRV) value of at least 18% lower than the fully dewaxed fraction using only solvent dewaxing when blended into a finished lubricating oil, wherein said lube oil boiling range feedstream is selected from raffinates, partially solvent dewaxed oils, deasphalted oils, distillates, vacuum gas oils, coker gas oils, foots oil, and dewaxed oils and c) adding the lube basestock to at least a second basestock and at least one additive, the second basestock being different from the first basestock.

10. The process according to claim 9, wherein the reaction product is fractionated in order to separate at least the lube basestock.

11. The process according to claim 9, wherein said hydrodewaxing catalyst further comprises at least one metal hydrogenation component, which is selected from Group VI metals, Group VIII metals, or mixtures thereof.

12. The process according to claim 9, wherein said process further comprises: a) contacting a lube oil boiling range feedstream in the presence of a hydrogen-containing treat gas with a hydroprocessing catalyst in a hydroprocessing reaction stage operated under effective hydroprocessing conditions thereby producing a hydroprocessed reaction product comprising a hydroprocessing stage gaseous product and a hydroprocessing stage liquid product comprising a hydroprocessed lube oil product; and b) conducting said hydroprocessed reaction product to said solvent dewaxing stage.

13. The process according to claim 12, wherein said hydroprocessing catalyst and said effective hydroprocessing conditions are selected to achieve hydrocracking of the lube oil boiling range feedstream; hydrotreating of the lube oil boiling range feedstream to remove heteroatoms; and/or hydrogenation of aromatics in the lube oil boiling range feedstream.

14. The process according to claim 9, wherein said process further comprises: a) solvent extracting said lube oil boiling range feedstream in a solvent extraction zone with an extraction solvent under conditions effective at producing at least an aromatics-lean raffinate solution containing extraction solvent; b) removing at least a portion of the extraction solvent from the aromatics-lean raffinate solution to produce at least a lube oil boiling range raffinate feedstream; and c) conducting said lube oil boiling raffinate feedstream to the solvent dewaxing stage.

15. The process according to claim 14, further comprising hydrotreating the lube oil boiling raffinate feedstream before solvent dewaxing.

16. The process according to claim 9, wherein the first basestock has a kinematic viscosity less than that of the second basestock, the kinematic viscosity being measured at about 100° C.

17. The process according to claim 9, wherein the lubricating oil has a pour point of less than about 0° C. and an MRV less than about 75,000 cP.

* * * * *